United States Patent
Kitareewan et al.

(10) Patent No.: US 8,124,371 B2
(45) Date of Patent: Feb. 28, 2012

(54) COMPOSITIONS AND METHODS FOR DESTABILIZING LYSOSOMES TO INCREASE ONCOGENIC OR ABERRANT PROTEIN DEGRADATION

(75) Inventors: Sutisak Kitareewan, Ordford, NH (US); Roger Sloboda, Hanover, NH (US); Ethan Dmitrovsky, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 1127 days.

(21) Appl. No.: 10/564,070

(22) PCT Filed: Jul. 30, 2004

(86) PCT No.: PCT/US2004/024611
§ 371 (c)(1),
(2), (4) Date: Mar. 3, 2006

(87) PCT Pub. No.: WO2005/016196
PCT Pub. Date: Feb. 24, 2005

(65) Prior Publication Data
US 2006/0228425 A1   Oct. 12, 2006

Related U.S. Application Data

(60) Provisional application No. 60/492,402, filed on Aug. 4, 2003.

(51) Int. Cl.
*C12Q 1/37* (2006.01)
*C12Q 1/34* (2006.01)
(52) U.S. Cl. .......................... 435/23; 435/18
(58) Field of Classification Search ............ None
See application file for complete search history.

(56) References Cited

U.S. PATENT DOCUMENTS

| 5,242,932 A | 9/1993 | Gandy et al. ............ 514/313 |
| 5,989,803 A | 11/1999 | Tabas et al. ............. 435/4 |
| 2002/0094958 A1 | 7/2002 | Bahr ....................... 514/18 |

OTHER PUBLICATIONS

Ikezoe et al. Amyloid-Beta Accumulation Caused by Chloroquine Injections Precedes Er Stress and Autophagosome Formation in Rat Skeletal Muscle; Acta Neuropathol, vol. 117 (2009) pp. 575-582.*
Schutt et al. Detergenzienwirkung Des Lipofuszin-Retinoidbestandteils A2-E in Retinalen Pigmentepithelzellen; Ophthalmologe, vol. 99 (2002) pp. 861-865.*
Ollinger, K and Brunk, U.T. Cellular Injury by Oxidative Stress is Mediated Through Lysosomal Damage; Free Radical Biology and Medicine, vol. 19, No. 5 (1995) pp. 565-574.*
Weeks, J and Svendsen, C. Neutral Red Retention by Lysosomes From Earthworm (*Lumbricus rubellus*) Coelomocytes: A Simple Biomarker of Exposure to Soil Copper; Environmental Toxicology and Chemistry, vol. 15, No. 10 (1996) pp. 1801-1805.*
Yoshida et al. Accelerated Degradation of PML-Retinoic Acid Receptor Alpha (PML-RARA) Oncoprotein by All-Trans-Retinoic Acid in Acute Promyelocytic Leukemia: Possibe Role of Proteasome Pathway; Cancer Research, vol. 56 (1996) pp. 2945-2948.*
Bard et al. Toxicity of Anti-Carcinogenic Retinoids in Organ Culture; British Journal of Cancer, vol. 35 (1977) pp. 115-119.*
Adamson et al. All-Trans-Retinoic Acid Pharmacology and Its Impact on the Treatment of Acute Promyelocytic Leukemia; The Oncologist, vol. 1 (1996) pp. 305-314.*

* cited by examiner

*Primary Examiner* — Rebecca Prouty
*Assistant Examiner* — Paul Martin
(74) *Attorney, Agent, or Firm* — Licata & Tyrrell P.C.

(57) ABSTRACT

The present invention relates to compositions for destabilizing lysosomes to increase the degradation of oncogenic or aberrant proteins for the prevention or treatment of disease. Methods for identifying agents which destabilize lysosomes are also provided as are agents identified in accordance with the screening method.

1 Claim, 1 Drawing Sheet

COMPOSITIONS AND METHODS FOR DESTABILIZING LYSOSOMES TO INCREASE ONCOGENIC OR ABERRANT PROTEIN DEGRADATION

CROSS-REFERENCE TO RELATED APPLICATIONS

This is application is a 371 of PCT/US04/24611 filed Jul. 30, 2004 which claims benefit of U.S. Provisional application 60/492,402 filed Aug. 4, 2003.

INTRODUCTION

This invention was supported in part by funds from the U.S. government (NIH Grant No. RO1-CA62275) and the U.S. government may therefore have certain rights in the invention.

BACKGROUND OF THE INVENTION

In acute promyelocytic leukemia (APL), the t(15;17) translocation fuses a nuclear receptor, RARα, to a nuclear matrix protein, PML (de Thé, et al. (1991) Cell 66:675-684). Transgenic mice expressing PML/RARα show impaired neutrophilic differentiation and develop leukemia, demonstrating that expression of the fusion protein initiates this malignancy (Brown, et al. (1997) Proc. Natl. Acad. Sci. USA 94:2551-2556). PML/RARα impairs both nuclear receptor-induced differentiation and PML-triggered apoptosis, likely accounting for the differentiation block and the unrestrained growth of the leukemic cells (Quignon, et al. (1997) Biochim. Biophys. Acta 1333:M53-M61; Lallemand-Breitenbach, et al. (1999) J. Exp. Med. 189:1043-1052). Expression of PML/RARα leads to accumulation in affected cases of immature promyelocytes in the bone marrow and peripheral blood. Inhibition of the retinoic acid response appears to involve the stabilization of corepressor proteins-histone deacetylase complexes on retinoic acid response elements (Lin, et al. (1998) Nature (London) 391:811-814; Grignani, et al. (1998) Nature (London) 391:815-818; He, et al. (1998) Nat. Genet. 18:126-135; Guidez, et al. (1998) Blood 91:2634-2642). The PML protein, which is localized on nuclear subdomains (PML nuclear bodies), has growth-suppressive and proapoptotic properties (Koken, et al. (1994) EMBO J. 13:1073-1083; Dyck, et al. (1994) Cell 76:333-343; Weis, et al. (1994) Cell 76:345-356; Mu, et al. (1994) Mol. Cell. Biol. 14:6858-6867; Quignon, et al. (1998) Nat. Genet. 20:259-265; Wang, et al. (1998) Nat. Genet. 20:266-272; Daniel, et al. (1993) Blood 82:1858-1867; Koken, et al. (1995) Oncogene 10:1315-1324). PML/RARα expression delocalizes nuclear body proteins, which has been proposed to account for apoptosis resistance (Grignani, et al. (1993) Cell 74:423-431).

Retinoic acid promotes differentiation of APL cells, causing degradation of PML/RARα and inducing clinical remissions in patients (Huang, et al. (1988) Blood 72:567-572). Degradation of PML/RARα after retinoic acid-treatment occurs through proteasome—as well as caspase-dependent pathways (Zhu, et al. (1999) Proc. Natl. Acad. Sci. USA 96:14807-14812). Arsenic trioxide also induces remissions, through combined induction of apoptosis and differentiation (Chen, et al. (1996) Blood 88:1052-1061). Both retinoic acid and arsenic trioxide treatments trigger PML/RARα degradation and nuclear body restoration (Zhu, et al. (1997) Proc. Natl. Acad. Sci. USA 94:3978-3983; Yoshida, et al. (1996) Cancer Res. 56:2945-2948; Muller, et al. (1998) EMBO J. 17:61-70; Raelson, et al. (1996) Blood 88:2826-2832), suggesting that the therapeutic action of these two drugs could be due to the down-regulation of the oncogenic fusion protein. However, data to support this hypothesis are conflicting (Nervi, et al. (1998) Blood 92:2244-2251; Fanelli, et al. (1999) Blood 93:1477-1481). Retinoic acid resistant, APL cases can occur and the trivalent form of arsenic has been used successfully in the treatment of these cases. It has been suggested that PML/RARα degradation is most likely responsible for the cross-facilitation of retinoic acid and arsenic trioxide effects (Lallemand-Breitenbach, et al. (1999) supra; Gianni, et al. (1998) Blood 91:4300-4310).

U.S. patent application Ser. No. 10/056,666 teaches compounds and methods of use thereof for modulating lysosome function wherein the compounds enhance the enzymatic capacity of lysosomes to suppress neuropathogenesis.

SUMMARY OF THE INVENTION

The present invention relates to a method for identifying an agent which destabilizes lysosomes to increase oncogenic or aberrant protein degradation. The method involves the steps of contacting a lysosome or a cell containing a lysosome with a test agent and detecting whether the test agent destabilizes the lysosome. In one embodiment, an agent which destabilizes lysosomes encompasses chloroquine or a derivative thereof.

The present invention also relates to a method for increasing oncogenic or aberrant protein degradation in cells. The method involves the steps of contacting cells with an effective amount of an agent which destabilizes lysosomes thereby increasing the degradation of oncogenic or aberrant proteins. In another embodiment of the present invention, an agent which destabilizes lysosomes is arsenic, chloroquine, or a derivative or a combination thereof as well as with the differentiation agent, all-trans-retinoic acid.

The present invention further relates to a method for treating a disease or condition associated with an oncogenic or aberrant protein. This method involves the steps of administering to a patient in need of treatment an effective amount of an agent which destabilizes lysosomes so that oncogenic or aberrant proteins degradation is increased thereby treating the disease or condition associated with the oncogenic or aberrant protein. In a further embodiment of the present invention, an agent which destabilizes lysosomes is arsenic, chloroquine, or a derivative or a combination thereof as well as with the differentiation agent, all-trans-retinoic acid.

DETAILED DESCRIPTION OF THE INVENTION

A novel pharmacological pathway that destabilizes lysosomes and targets oncogenic or other aberrant proteins for destruction has now been identified. The results provided herein show that arsenic can act through a previously unknown mechanism that targets PML/RARα for degradation by rapidly destabilizing lysosomes. Destabilization leads to release of lysosomal enzymes, which triggers PML/RARα degradation in a variety of cell types.

By way of illustration, arsenic was applied to APL, retinoic acid-sensitive NB4-S1 cells and found to rapidly (within 2 hours) destabilize lysosomes in these leukemic cells as compared to untreated cells in an assay using a lysosome-specific targeting dye and confocal microscopy. SDS-PAGE and immunoblot analyses of cell lysates derived from NB4-S1 APL cells showed that lysosomal protein esterase and cathepsin B were detectable in the cytosolic fraction as early as 5 and 30 minutes, respectively, after 1 µM arsenic treatment. Conversely, cytochrome c (an activator of caspase-induced apoptosis) was not detected in the cytosol until 96 hours.

Cell lysates of NB4-S1 cells, either treated for 72 hours with arsenic (1 µM) or left untreated, were obtained using a mild-lysis buffer that supported lysosomal enzymatic activity. In vitro degradation assays were performed using these lysates and HA-tagged PML/RARα was used as a target for degradation. In this assay, PML/RARα was rapidly degraded in the reaction mixture containing cell lysates of arsenic-treated NB4-S1 cells and not the untreated cell lysates. Lysosomal protease inhibitors blocked PML/RARα degradation, however, the proteasome inhibitor ALLN and the caspase inhibitor zVAD did not block PML/RARα degradation. These results indicated that arsenic triggered the destabilization of lysosomal bodies which sequester degradative enzymes thereby resulting in the degradation of the PML/RARα fusion protein.

Consistent with these findings, isolated lysosomes from NB4 APL cells exhibited degradation in vitro upon arsenic treatment. This arsenic-activated degradation program was also engaged by non-leukemic cells. Briefly, wild-type cystic fibrosis protein (CFTR) engineered to over-express in dog kidney epithelial cells (MDCK) was observed to be degraded by cell content of COS that has been exposed to arsenic. Accordingly, this lysosome-dependent degradative pathway can be employed as a general therapeutic target for the destruction of oncogenic (e.g., PML/RARα) or aberrant (e.g., CFTR) proteins in the prevention and treatment of cancer or other diseases which are associated with said proteins. Further, lysosome destabilization can be used to identify other small molecule activators which, like arsenic, would have therapeutic activity via induced destabilization of lysosomes that would in turn eliminate oncogenic or other aberrant proteins by triggering their destruction.

Figure 1A:
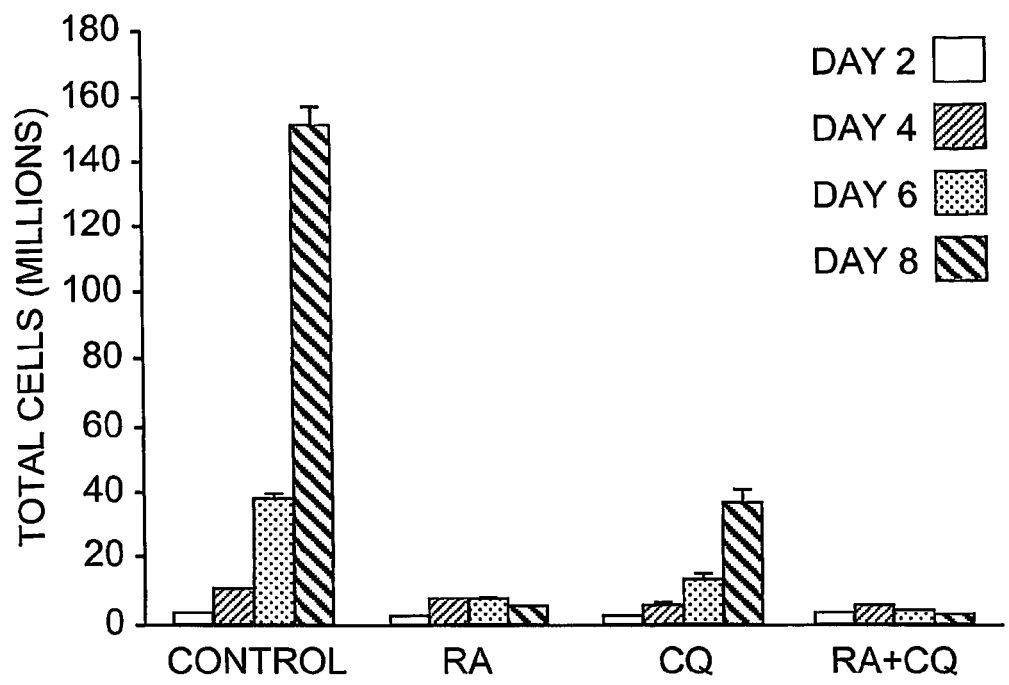
FIG. 1 shows the growth suppressive profile of chloroquine (CQ). Rentinoic acid-sensitive NB4-S1 APL cells (FIG. 1A) and Retinoic acid-resistant NB4-R1 APL cells (FIG. 1B) were cultured in the absence (control) and presence of retinoic acid (0.1 µM), chloroquine (20 µM), and the combination of retinoic acid (0.1 µM) and chloroquine (20 µM) at the indicated times. Three independent experiments were conducted. Cells were counted using a Coulter cell counter and the mean values are displayed along with standard deviations (error bars).
Figure 1B:
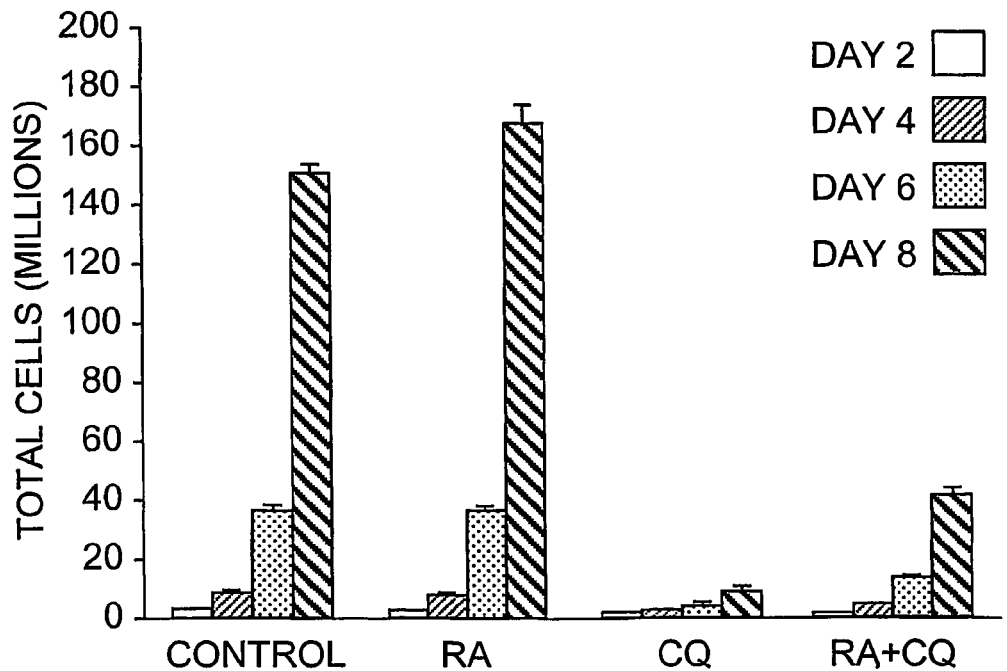

To identify other agents which destabilize lysosomes, APL cells were contacted with test agents and the ability of the test agent to induce cell death was evaluated. To illustrate, known lysosomal targeting drugs such as imipramine, chloroquine, and N-Octyl-D-erythro-spingosine were each tested for the ability to suppress growth of retinoic acid-sensitive and retinoic acid-resistant cells, alone or in combination with retinoic acid. Of the agents tested, the anti-malarial agent chloroquine exhibited the most prominent growth suppressive activity. Imipramine and N-octyl-D-erythro-sphingosine also have some growth suppressive activity toward retinoic acid-sensitive cells. It is contemplated that derivatives of these compounds may have activity also as anti-leukemic agents. Chloroquine (20 µM) had an additive growth inhibitory effect in retinoic acid-sensitive cells when combined with retinoic acid at 0.1 µM, a concentration of retinoic acid that is 10-fold lower than the amount used clinically (FIG. 1A). Further, chloroquine alone suppressed growth of retinoic acid-resistant cells (FIG. 1B). In addition to APL cells, chloroquine also exhibited a growth suppressive activity on non-APL myeloid leukemic cells including multi-drug resistant cell lines such as K562 and HL60/MX2. These results indicate chloroquine, or a derivative thereof, is useful alone or in combination with low dose retinoic acid in anti-leukemic therapy and can, in general, be useful for destabilizing lysosomes for the prevention or treatment of diseases associated with an oncogenic or aberrant protein.

Chloroquine is an effective and clinically well-tolerated drug used in malaria treatment since 1950. Because chloroquine is a weak base, it accumulates in the lysosomes of eukaryotic organisms such as the malaria parasite. Chloroquine accumulation raises the pH of the lysosome which in turn inhibits the polymerization of toxic ferriproporphyrin IX leading to the death of the malaria parasite. Thus, the mechanism(s) of growth suppressive activity of chloroquine in APL cell lines was analyzed. For this analysis, cells were either untreated, treated with retinoic acid (0.1 µM) or treated with chloroquine (20 µM) for 6 days. Cell differentiation was evaluated using a nitroblue tetrazolium reduction assay, wherein the presence blue formazan deposits under light microscopy is indicative of differentiated cells. Further, apoptosis was evaluated using Hoechst staining of nuclear DNA wherein the DNA was characterized morphologically by nuclear condensation and fragmentation of chromosomes. In these studies, it was found that chloroquine does not induce differentiation in APL NB4-S1 cells, however, chloroquine does suppress NB4-S1 cell growth via induction of apoptosis. The induction of apoptosis in NB4-S1 cells by 20 µM chloroquine treatment was found to be exposure time-dependent (see Table 1). Similar results were observed when retinoic acid-resistant NB4-R1 APL cells were cultured with chloroquine.

TABLE 1

| Treatment | % Apoptosis |
|---|---|
| Untreated Control | 3 |
| Chloroquine - 24 Hours | 16 |
| Chloroquine - 48 Hours | 20 |
| Chloroquine - 72 Hours | 30 |

Retinoic acid-sensitive, NB4-S1 APL cells were left or treated 20 µM chloroquine for 24, 48, or 72 hours and then stained with Hoechst stain before analysis with a fluorescence microscope. The percentage of apoptotic cells was determined. This experiment was performed independently three times and three random fields were selected to assess the percentage of apoptotic cells.

Accordingly, these results indicate that an apoptotic assay can be used to identify other lysosomal targeting agents which can be used alone or in combination with other agents such as retinoic acid or arsenic in the treatment of APL, non-APL, or other malignancies or diseases associated with an oncogenic or aberrant protein. Therefore, the present invention relates to a method for identifying an agent that destabilizes lysosomes to increase oncogenic or aberrant protein degradation. The method involves the steps of contacting an isolated lysosome or cell containing a lysosome with a test agent and detecting whether the test agent destabilizes the lysosome.

It is contemplated that any cell containing a lysosome can be used in the assay of the invention including but not limited to cells retained in tissue, cell clusters and individually isolated cells such as mammalian cells, plant cells and the like. Likewise, a lysosome for use in the screening method of the present invention can be isolated from any cell using standard methods including, but not limited to fractionation of cell homogenates on PERCOLL™ or sucrose gradients (see, e.g., Lindmark, et al. (1994) *J. Leukocyte Biol.* 66:634-643). Further, it is contemplated that a cell used in the assay of the present invention may or may not express an oncogenic or aberrant protein.

Lysosome destabilization can be detected using the methods disclosed herein (e.g., cell death) or any other well-established method for detecting or measuring whether a lysosome is intact or destabilized. For example, the release of lysosomal proteins such as cathepsin D or L, alanine aminopeptidase, leucine aminopeptidase, N-acetyl-β-glucosaminidase, lysosomal arylesterase or lysosomal lipase into the cytosol or into the medium is indicative of lysosomal destabilization. Methods for detecting these proteins are well-known in the art and can include detecting enzymatic activity or immunodetection.

Further, destabilization of lysosomes can be detected by vital staining of lysosomes using a vital dye such as LYSOTRACKER™ (Molecular Probes) which stains lysosomes on the basis of their acidic pH.

Identification of a lysosomal destabilization agent can be performed in any format that allows rapid preparation and processing of multiple reactions such as in, for example, multi-well plates of the 96-well variety. Stock solutions of the test agents as well as cells or lysosomes and assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotomers, calorimeters, and fluorimeters, and devices that measure the decay of radioisotopes.

The assay of the invention can be used to screen libraries of synthetic or natural compounds including small molecule or combinatorial libraries produced by any of the techniques already in the public domain or otherwise known to those skilled in the art. Because of their large size, these libraries are likely sources of lead agents since they can contain from $10^7$ to $10^{10}$ chemical entities.

Agents which can be screened in accordance with the screening assay provided herein encompass numerous chemical classes, though typically they are organic molecules, generally small organic compounds having a molecular weight of more than 100 and less than about 2,500 daltons (e.g., cyclical carbon or heterocyclic structures and/or aromatic or polyaromatic structures substituted with one or more functional groups). Agents can also be found among biomolecules including peptides, antibodies, carbohydrates, fatty acids, steroids, purines, pyrimidines, lipids, synthetic or semi-synthetic chemicals, and purified natural products derivatives, or structural analogs or combinations thereof.

A variety of other reagents can also be included in the screening assay of the invention. Such reagents include salts, neutral proteins (e.g., albumin), mild detergents, etc. and can be used to facilitate optimal assay conditions. Also, reagents that otherwise improve the efficiency of the assay, such as anti-microbial agents and the like can also be used.

As disclosed herein, the assay method of the present invention identified chloroquine as an exemplary lysosomal destabilizing agents. It is contemplated that chloroquine as well as derivatives, analogs, or enantiomers of chloroquine, or combinations thereof, will be useful for destabilizing lysosomes to increase the degradation of oncogenic or aberrant proteins. Further, chloroquine or other lysosomal destabilizing agents identified in accordance with the assay method of the present invention can be used alone or in combination with each other or with arsenic or retinoic acid to destabilize lysosomes to increase degradation of oncogenic or aberrant proteins.

When arsenic is employed, it can be used in an inorganic as well as organic form (e.g., trivalent or pentavalent) Moreover, arsenic-containing compounds such as methyl and phenyl arsenates are further contemplated.

Retinoic acids useful in destabilizing lysosomes include, but are not limited to, retinoic acids, 9-cis-retinoic acid and 13-cis-retinoic acid and other retinoids such as retinol (Vitamin A alcohol), retinal (Vitamin A aldehyde), retinyl acetate, and retinyl palmitate or mixtures thereof. Suitable synthesis techniques for these retinoic acids and retinoids are well-known in the art.

When a chloroquine compound is used to destabilize lysosomes, it can be chloroquine, chloroquine phosphate, and hydroxychloroquine, chloroquine diphosphate, chloroquine sulphate, hydroxychloroquine sulphate, or enantiomers, derivatives or mixtures thereof. As defined herein hydroxychloroquine is a beta-hydroxylated N-ethyl substituent of chloroquine.

Chloroquine (7-chloro-4-(4-diethylamino-1-methylbutylamino) quinoline) (The Merck Index, p. 2220, 1996) is a synthetically manufactured anti-malarial containing a quinoline nucleus. Suitable synthesis techniques for chloroquine and its derivatives are well-known in the art. For example, see, U.S. Pat. No. 2,233,970. A number of chloroquine derivatives that are useful in the methods described herein are well-known. For example, suitable agents and methods for synthesizing the same are described in U.S. Pat. Nos. 6,417,177; 6,127,111; 5,639,737; 5,624,938; 5,736,557; 5,596,002; 5,948,791; 2,653,940 and 4,421,920.

Examples of suitable chloroquine derivatives include, but are not limited to, 7-chloro-4-(4-diethylamino-1-methylbutylamino)quinoline (chloroquine); 7-hydroxy-4-(4-diethylamino-1-methylbutylamino)quinoline; chloroquine phosphate; 7-chloro-4-(4-diethylamino-1-butylamino)quinoline (desmethylchloroquine); 7-hydroxy-4-(4-diethylamino-1-butylamino)quinoline; 7-chloro-4-(1-carboxy-4-diethylamino-1-butylamino)quinoline; 7-hydroxy-4-(1-carboxy-4-diethylamino-1-butylamino)quinoline; 7-chloro-4-(1-carboxy-4-diethylamino-1-methylbutylamino)quinoline; 7-hydroxy-4-(1-carboxy-4-diethylamino-1-methylbutylamino)quinoline; 7-chloro-4-(4-ethyl-(2-hydroxyethyl)-amino-1-methylbutylamino) quinoline (hydroxychloroquine); 7-hydroxy-4-(4-ethyl-(2-hydroxyethyl)-amino-1-methylbutylamino) quinoline; hydroxychloroquine phosphate; 7-chloro-4-(4-ethyl-(2-hydroxyethyl)-amino-1-butylamino)quinoline (desmethyl-hydroxychloroquine); 7-hydroxy-4-(4-ethyl-(2-hydroxyethyl)-amino-1-butylamino)quinoline; 7-chloro-4-(1-carboxy-4-ethyl-(2-hydroxyethyl)-amino-1-butylamino)quinoline; 7-hydroxy-4-(1-carboxy-4-ethyl-(2-hydroxyethyl)-amino-1-butylamino) quinoline; 7-chloro-4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino) quinoline; 8-[(4-aminopentyl)amino]-6-methoxydihydrochloride quinoline; 1-acetyl-1,2,3,4-tetrahydroquinoline; 8-[4-aminopentyl) amino]-6-methoxyquinoline dihydrochloride; 1-butyryl-1,2,3,4-tetrahydroquinoline; 7-chloro-2-(o-chlorostyryl)-4-[4-diethylamino-1-methylbutyl]aminoquinoline phosphate; 3-chloro-4-(4-hydroxy-α,α'-bis(2-methyl-1-pyrrolidinyl)-2, 5-xylidinoquinoline; 4-[(4-diethylamino)-1-methylbutyl) amino]-6-methoxyquinoline; 3,4-dihydro-1(2H)-quinoline-carboxyaldehyde; 1,1'-pentamethylenediquinoleinium diiodide; and 8-quinolinol sulfate, enantiomers thereof, as well as suitable pharmaceutical salts thereof.

Chloroquine and hydroxychloroquine are racemic mixtures of (−)- and (+)-enantiomers. The (−)-enantiomers are also known as (R)-enantiomers (physical rotation) and 1-enantiomers (optical rotation). The (+)-enantiomers are also known as (S)-enantiomers (physical rotation) and r-enantiomers (optical rotation). The metabolism of the (+)- and the (−)-enantiomer of chloroquine are described in Augustijins and Verbeke (1993) *Clin. Pharmacokin.* 24(3): 259-69; Augustijins, et al. (1999) *Eur. J. Drug Metabol. Pharmacokin.* 24(1):105-8; DuCharme and Farinotti (1996) *Clin. Pharmacokin.* 31(4):257-74. Desirably, a (−)-enantiomer is used. The enantiomers of chloroquine and hydroxychloroquine can be prepared by procedures known to the art.

The results provided herein show that oncogenic or aberrant proteins can be actively degraded by lysosomal destabilization. Accordingly, the present invention relates to a method for increasing oncogenic or aberrant protein degradation in cells by contacting cells with an effective amount of an agent which destabilizes lysosomes. An effective amount of an agent which destabilizes lysosomes in the context of this method of the invention is an amount which causes a 30%, 40%, 50%, 60%, 70%, 80%, 90%, 95%, 98%, or 100% decrease in the amount of an oncogenic or aberrant protein in a cell when compared to otherwise same conditions wherein the active agent is not present.

As used herein, an oncogenic protein is a protein expressed by tumor cells which promotes or allows the uncontrolled growth of cancer. Expression of such oncogenic proteins can be inherited or caused by an environmental exposure to carcinogens. A normal protein or protooncoprotein can become oncogenic by relatively small modifications to the original function. There are two basic types of activation which convert a protooncoprotein into an oncogenic protein: a mutation within a protooncogene which results in an increase in protein activity, a loss of protein regulation, or creation of a hybrid protein; or an increase in protein concentration caused by an increase in protein expression, an increase in protein stability, or gene duplication. Oncogenes can be growth factors as well as protein kinases. Examples of oncogenic proteins which can be degraded in accordance with the method of the present invention are well-known to the skilled artisan and include, but are not limited to PML/RARα, HER-2/neu, Ras protein, c-Jun, c-Myc, the protein tyrosine kinase src, hTert, and Bcl-2.

Aberrant proteins which can be degraded in accordance with the method of the present invention include proteins whose structure or solubility leads to the formation of an aggregation-prone product and cause disease. Exemplary aberrant proteins and their associated conditions include, but are not limited to, Alzheimer's amyloid peptide (Aβ), SOD1, presenillin 1 and 2, α-synuclein, amyloid A, amyloid P, CFTR, transthyretin, amylin, lysozyme, gelsolin, p53, rhodopsin, insulin, insulin receptor, fibrillin, α-ketoacid dehydrogenase, collagen, keratin, PRNP, immunoglobulin light chain, atrial natriuretic peptide, seminal vesicle exocrine protein, β2-microglobulin, PrP, precalcitonin, ataxin 1, ataxin 2, ataxin 3, ataxin 6, ataxin 7, huntingtin, androgen receptor, CREB-binding protein, dentatorubral pallidoluysian atrophy-associated protein, maltose-binding protein, ABC transporter, glutathione-S-transferase, and thioredoxin.

Agents which destabilize lysosomes to increase oncogenic or aberrant protein degradation are further useful for in the prevention or treatment of diseases or conditions associated with the expression of an oncogenic or aberrant protein. Thus, the present invention relates to a method for preventing or treating such diseases or conditions. The method involves administering to a patient in need of treatment an effective amount of an agent which destabilizes lysosomes. A patient in need of treatment can include an individual having or suspected of having a disease or condition associated with an oncogenic or aberrant protein.

Exemplary oncogenic or aberrant proteins are provided herein and the diseases or conditions associated with these proteins as well as the signs and symptoms of the diseases or conditions are well-known to the skilled artisan. For example, it is well-established in the art that amyloid peptide (Aβ), presenillin 1 and 2, α-synuclein, amyloid A, and amyloid P are associated with Alzheimer's disease; PrP is associated with Mad Cow and Creutzfeldt-Jakob Disease; and CFTR is associated with cystic fibrosis.

It is contemplated that an individual having or suspected of having a disease or condition associated with an oncogenic or aberrant protein may or may not exhibit a sign or symptom of the disease or condition. Individuals who do not exhibit a sign or symptom of the disease or condition but who are at risk of having the disease or condition include those with a family member or family history of having such a disease or condition associated with an oncogenic or aberrant protein or who have inherited an abnormal gene. Examples of such inherited conditions and diseases are well-established in the art and can be routinely identified by the skilled clinician and in screening assays.

In the context of the method of treatment of the present invention, an effective amount of an agent which destabilizes lysosomes is an amount sufficient to effect beneficial or desired results, including clinical results, and, as such, an effective amount of the agent is one which provides an alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. Treatment can also mean prolonging survival as compared to expected survival if not receiving treatment. As will be understood by the skilled artisan, the signs or symptoms of the disease or condition can vary with the stage of the disease or condition and the signs or symptoms associated with various stages are well-known to the skilled clinician. See, for example, The American Joint Committee on Cancer Staging Manual, Sixth Edition.

Agents used in accordance with the methods of the invention can be conveniently administered in a pharmaceutical composition containing the active agent in combination with a suitable carrier. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippingcott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the patient.

Examples of materials which can serve as pharmaceutically-acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Agents of the invention can be administered locally or systemically via any route including, but not limited to, oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal and inhalation administration, administration to the liver by intraportal delivery, as well as direct organ injection (e.g., into the liver, into the brain for delivery to the central nervous system) or direct tumor or intralesional injection. The most suitable route in any given case will depend on the nature and severity of the condition being treated and on the nature of the particular agent which is being used.

For injection, the carrier will typically be a liquid, such as sterile pyrogen-free water, pyrogen-free phosphate-buffered saline solution, bacteriostatic water, or CREMOPHOR (BASF, Parsippany, N.J.). For other methods of administration, the carrier can be either solid or liquid.

For oral therapeutic administration, the active agent can be combined with one or more carriers and used in the form of ingestible tablets, buccal tablets, troches, capsules, elixirs, suspensions, syrups, wafers, chewing gums, foods and the like. Such compositions and preparations should contain at least 0.1% of active agent. The percentage of the agent and preparations can, of course, be varied and can conveniently be between about 0.1 to about 100% of the weight of a given unit dosage form. The amount of active agent in such compositions is such that an effective dosage level will be obtained.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac or sugar and the like.

A syrup or elixir can contain the active agent, sucrose or fructose as a sweetening agent, methyl and propylparabens as preservatives, a dye and flavoring such as cherry or orange flavor. Of course, any material used in preparing any unit dosage form should be substantially non-toxic in the amounts employed. In addition, the active agents can be incorporated into sustained-release preparations and devices including, but not limited to, those relying on osmotic pressures to obtain a desired release profile.

Agents for parenteral administration can be formulated to contain sterile aqueous and non-aqueous injection solutions of the active agent, which preparations are generally isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose or multi-dose containers, for example sealed ampules and vials, and can be stored in a freeze-dried (lyophilized) condition requiring only the addition of the sterile liquid carrier, for example, saline or water-for-injection immediately prior to use.

Prolonged absorption of the injectable compositions can be brought about by including in the composition an agent which delays absorption, for example, monostearate salts and gelatin. Moreover, a Grm1 inhibitor or activator can be administered in a time-release formulation, for example in a composition which includes a slow release polymer. The active compounds can be prepared with carriers that protect the agent against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Formulations suitable for topical application to the skin can take the form of an ointment, cream, lotion, paste, gel, spray, aerosol, oil or other pharmaceutical formulation which accomplishes direct contact between the active agent and the skin. Topical formulations can also be prepared which are suitable for occlusive therapy.

Formulations in the forms of ointments, creams, lotions and pastes can generally have carriers in the forms of oleaginous bases (e.g., White Petrolatum and White Ointment); absorption bases formed by adding a water-in-oil emulsifying agent to an oleaginous base (e.g., Hydrophilic Petrolatum, AQUABASE, and AQUAPHOR); water-in-oil emulsion bases, prepared by adding water to an absorption base (e.g., HYDROCREAM, EUCERIN, NIVEA, and Cold Cream); oil-in-water emulsion bases (e.g., DERMABASE, UNIBASE, VELVACHOL, and hydrophilic ointment); and water soluble bases (e.g., polyethylene glycol ointment such as PEG 400-600 G or PEG 3350-400 G). Suitable carriers to produce a spray, gel, or aerosol are well-known in the art.

The selected dosage level will depend upon a variety of factors including the activity of the particular agent of the present invention employed, the route of administration, the time of administration, the rate of excretion or metabolism of the particular compound being employed, the duration of the treatment, other drugs, compounds and/or materials used in combination with the particular agent employed, the age, sex, weight, condition, general health and prior medical history of the patient being treated, and like factors well-known in the medical arts.

A physician or veterinarian having ordinary skill in the art can readily determine and prescribe the effective amount of the pharmaceutical composition required for prevention or treatment in an animal subject such as a human, agriculturally-important animal, pet or zoological animal. For example, a daily dose of chloroquine or derivative thereof can be about 0.5 mg/kg to about 50 mg/kg body weight or in the range of 1.0 mg/kg to about 10 mg/kg body weight.

To enhance activity and reduce toxicity and side effects, agents of the present invention can be administered in the form of prodrugs or alternatively be targeted to cells expressing oncogenic or aberrant proteins using methods well-known in the art. For example, a cell-surface targeting moiety can be covalently attached to the active agent via a biodegradable linker wherein the targeting Moiety specifically targets the active agent to the surface of a cell of interest and facilitates uptake into the cell. Exemplary targeting moieties for use in targeting cancer cells include peptide hormones such as bombesin, stomatostatin and luteinizing hormone-releasing hormone (LHRH) or analogs thereof. Cell-surface receptors for peptide hormones have been shown to be overexpressed in tumor cells (Schally (1994) *Anti-Cancer Drugs* 5:115-130; Lamharzi, et al. (1998) *Int. J. Oncol.* 12:671-675) and the ligands to these receptors are known tumor cell targeting agents (Grundker, et al. (2002) *Am. J. Obstet. Gynecol.* 187 (3):528-37; WO 97/19954). Carbohydrates such as dextran having branched galactose units (Ohya, et al. (2001) *Biomacromolecules* 2(3):927-33), lectins (Woodley (2000) *J. Drug Target.* 7(5):325-33), and neoglycoconjugates such as Fucalphal-2Gal (Galanina, et al. (1998) *Int. J. Cancer* 76(1): 136-40) can also be used as targeting moieties to treat, for example, colon cancer. It is further contemplated that an antibody or antibody fragment which binds to a protein or receptor, which is specific to a tumor cell, can be used as a cell-surface targeting moiety. Exemplary antibody targeting moieties include bispecific monoclonal antibodies composed of an anti-histamine-succinyl-glycine Fab' covalently coupled with an Fab' of either an anticarcinoembryonic antigen or an anticolon-specific antigen-p antibody (Sharkey, et al. (2003) *Cancer Res.* 63(2):354-63).

What is claimed is:

1. A method for identifying an agent that destabilizes lysosomes and increases oncogenic protein degradation; comprising: contacting a cancer cell expressing PML/RARα with an agent, wherein the agent is not retinoic acid, and
   i) detecting destabilization of the lysosomes of the cell by vital staining of lysosomes or release of lysosomal proteins into the cytosol; and
   ii) detecting an increases in lysosomal-dependent PML/RARα protein degradation, thereby identifying an agent that destabilizes lysosomes and increases oncogenic protein degradation.

* * * * *